US00PP22172P2

(12) United States Plant Patent
Radler

(10) Patent No.: US PP22,172 P2
(45) Date of Patent: Oct. 4, 2011

(54) SHRUB ROSE PLANT NAMED 'RADCARN'

(50) Latin Name: *Rosa hybrida*
Varietal Denomination: Radcarn

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/923,140

(22) Filed: Sep. 3, 2010

(51) Int. Cl.
*A01H 5/00* (2006.01)

(52) U.S. Cl. ..... Plt./102
(58) Field of Classification Search ..... Plt./102
See application file for complete search history.

*Primary Examiner* — Kent L Bell
(74) *Attorney, Agent, or Firm* — Buchanan Ingersoll & Rooney PC

(57) ABSTRACT

A new and distinct shrub rose plant is provided that abundantly and substantially continuously forms attractive double pink and white bi-colored blossoms. The plant exhibits vigorous vegetation and an upright and bushy growth habit. The foliage is ornamental dark green with a matte finish. A very light sweet fragrance is provided by the blossoms. The plant is well suited for growing as attractive ornamentation in parks and gardens.

1 Drawing Sheet

Botanical/commercial classification: *Rosa hybrida* / Shrub Rose Plant.

Varietal denomination: cv. Radcarn.

SUMMARY OF THE INVENTION

The new variety of *Rosa hybrida* shrub rose plant of the present invention was created during June 2001 at Greenfield, Wis., U.S.A., by artificial pollination wherein two parents were crossed which previously had been studied in the hope that they would contribute the desired characteristics. The female parent (i.e., the seed parent) was the 'Radrise' variety (non-patented in the United States). The male parent (i.e., the pollen parent) of the new variety was the 'Radsweet' variety (U.S. Plant Pat. No. 19,032). The parentage of the new variety can be summarized as follows:

'Radrise'×'Radsweet'.

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly and substantially continuously forms attractive double pink and white bi-colored blossoms,
(b) exhibits an upright and bushy growth habit,
(c) forms vigorous vegetation,
(d) forms attractive ornamental dark green foliage with a matte finish,
(e) exhibits good disease resistance, and
(f) is well suited for providing attractive ornamentation in the landscape.

A new rose variety is provided which bears attractive pink and white bi-colored blossoms combined with substantially continuous blooming and resistance to disease.

The new variety well meets the needs of the horticultural industry. It can be grown to advantage as ornamentation in parks, gardens, public areas, and in residential settings. The new variety is particularly well suited for providing attractive ornamentation in the landscape. The pink and white bi-colored blossoms contrast nicely with the dark green matte foliage.

The new variety of the present invention can be readily distinguished from its ancestors, and other comparative varieties such as the 'Radtkopink' variety (U.S. Plant Pat. No. 18,507). More specifically, while the growth habit of the new variety is similar to that of the 'Radtkopink' variety, the blossoms of the 'Radtkopink' variety are solid pink unlike the bi-colored blossoms of the new variety. The 'Radrise' female parent exhibits a larger shrub to climber growth habit and forms blossoms that commonly tend to remain partially closed during humid weather unlike those of the new variety. The 'Radsweet' male parent displays single blossoms having a darker pink coloration.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radcarn' and will be marketed in the United States under the PEPPERMINT POP trademark.

BRIEF DESCRIPTION OF THE PHOTOGRAPH

The accompanying photograph shows, as nearly true as it is reasonably possible to make the same in a color illustration of this character, a row of typical flowering specimens of the new variety. The illustrated rose plants of the new variety were approximately four years of age and were observed during June while growing outdoors near West Grove, Pa., U.S.A. The upright and bushy growth habit, abundance of bi-colored blossoms, and dark green foliage are illustrated.

DETAILED DESCRIPTION

The chart used in the identification of colors is that of The Royal Horticultural Society (R.H.S. Colour Chart), London, England. The description is based on the observation of two-year-old specimens of the new variety during July while growing outdoors in containers near West Grove, Pa., U.S.A.

Class: Landscape Shrub.

Plant:

*Height.*—Approximately 3.5 feet on average at the end of the growing season.

*Width.*—Up to approximately 3.5 feet on average at the end of one growing season.

*Habit.*—Upright and bushy.

Branches:

*Length.*—Commonly approximately 30 cm.

*Diameter.*—Commonly approximately 3 mm.

*Texture.*—Smooth with a few prickles.

*Color.*—Yellow-Green Group 144A.

*Thorns.*—Size: approximately 8 mm in length, approximately 4 mm in width at the base, and commonly Greyed-Red Group 180C in coloration.

Leaves:

*Leaflets.*—Number: 3, 5 and 7. Length: approximately 4.5 cm on average for a terminal leaflet, and approximately 2 cm on average for a lower leaflet. Width: approximately 3 cm on average at the widest point for a terminal leaflet, and approximately 1 cm on average at the widest point for a lower leaflet. Shape: with an acute apex and a cuneate base. Margins: denticulate. Texture: smooth on both surfaces, and ribbed on the under surface. Overall appearance: attractive ornamental dark green matte foliage. Color: upper surface: commonly Green Group 137A. under surface: commonly Green Group 137C.

*Petiole.*—Commonly approximately 1.5 cm in length on average, approximately 2 to 3 mm in diameter, and near Yellow-Green Group 145A in coloration.

Inflorescence:

*Number of flowers.*—Commonly singly or in clusters of approximately 3 blooms.

*Peduncle.*—Near Yellow-Green Group 146C with some Greyed-Orange Group 176B in coloration, commonly approximately 4 to 5 cm in length and commonly approximately 3 mm in diameter.

*Sepals.*—Shape: with an acuminate apex and a relatively smooth margin. Upper surface: smooth, and commonly between Yellow-Green Group 144A and Yellow-Green Group 144B in coloration. under surface: smooth and near Yellow-Green Group 144B in coloration. Size: commonly approximately 2 cm in length on average, and approximately 1 cm in width at the point of attachment. Number: five.

*Buds.*—Shape: ovoid. Length: approximately 2.2 cm on average as the calyx breaks. Diameter: approximately 2 cm as the calyx breaks. Color (when opening): Red-Purple Group 61D with some Yellow Group 5C at the base.

*Flower.*—Form: double. Diameter: approximately 10 cm on average when fully open. Depth: approximately 4 cm on average. Color (when opening begins): upper surface: bicolored, towards the apex Red Group 55B and Red Group 55C, and towards the base near Yellow-White Group 158C. under surface: near Red Group 56B. Color (at end of blooming): upper surface: bicolored, towards the apex near Greyed-Purple Group 186D, and towards the base near Yellow-White Group 158D. under surface: bicolored, towards the apex near Greyed-Purple Group 186D, and towards the base near Yellow-White Group 158D. Fragrance: very light sweet scent. Petal number: commonly approximately 45 on average. Petaloids: substantially ovoid in shape, approximately 2 cm in length, approximately 1.5 cm in width, commonly approximately 10 in number on average, and Red-Purple Group 61D in coloration commonly with some White Group 155A at the point of attachment and at the center. Petal shape: substantially ovoid, approximately 3 cm in length on average, approximately 2.2 cm in width on average, with relatively smooth margins, and the individual petals tend to slowly curl under to resemble a point at the apex as the blossoms mature. Petal drop: influenced by the level of humidity with the petals not always dropping cleanly. Stamen: approximately 120 on average, and regularly arranged about the pistils. Anthers: near Greyed-Orange Group 163B in coloration. Filaments: approximately 5 to 10 mm in length on average, and near Yellow Group 6A in coloration. Pistils: approximately 50 on average, separate and free. Receptacle: achenes commonly stand on the bottom and wall.

Development:

*Vegetation.*—Vigorous and strong.

*Blossoming.*—Abundant and substantially continuous during the growing season.

*Resistance to disease.*—Excellent with respect to Blackspot, Mildew, and Rust during observations to date.

*Formation of hips/seeds.*—None have been observed during observations to date.

I claim:

1. A new and distinct shrub rose plant characterized by the following combination of characteristics:

(a) abundantly and substantially continuously forms attractive double pink and white bi-colored blossoms, (b) exhibits an upright and bushy growth habit, (c) forms vigorous vegetation, (d) forms attractive ornamental dark green foliage with a matte finish, (e) exhibits good disease resistance, and (f) is well suited for providing attractive ornamentation in the landscape;

substantially as herein shown and described.

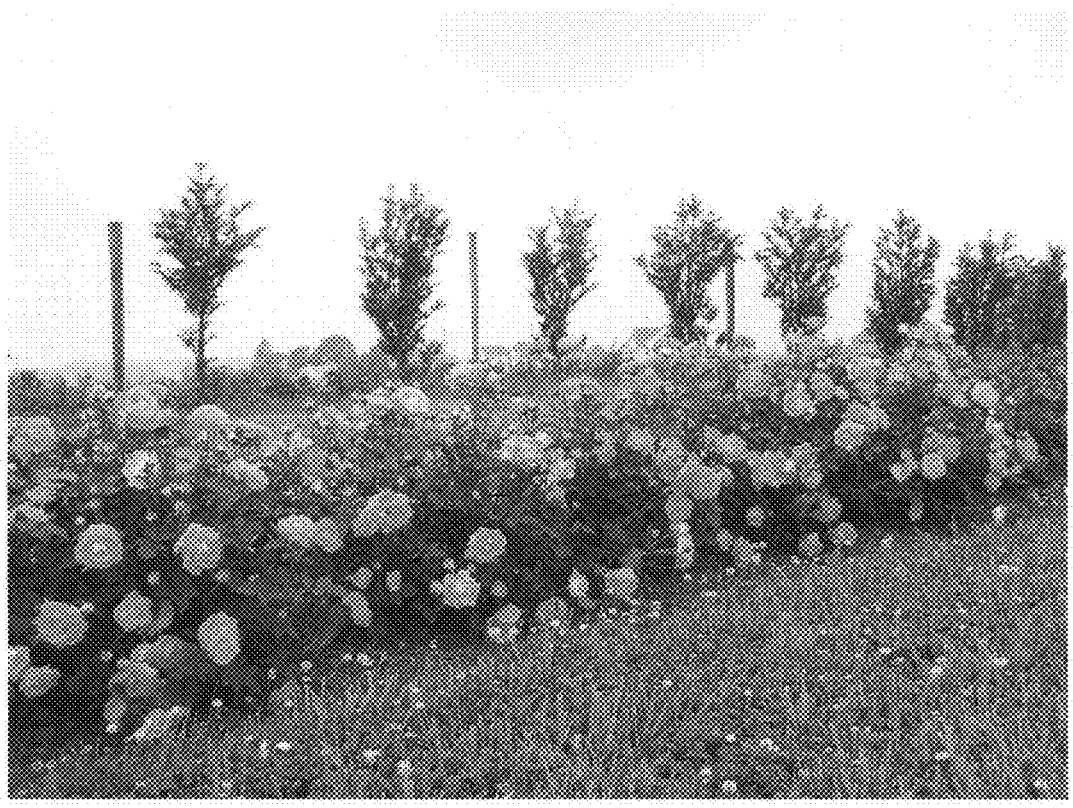

* * * * *